United States Patent [19]
Kresge et al.

[11] Patent Number: 5,231,235
[45] Date of Patent: Jul. 27, 1993

[54] PROCESS FOR PREPARING ETHERS

[75] Inventors: Charles T. Kresge, West Chester, Pa.; Quang N. Le, Cherry Hill; Wieslaw J. Roth, Sewell; Robert T. Thomson, Lawrenceville; Grant H. Yokomizo, Cherry Hill, all of N.J.

[73] Assignee: Mobil Oil Corp., Fairfax, Va.

[21] Appl. No.: 891,014

[22] Filed: Jun. 1, 1992

[51] Int. Cl.$^5$ .............................................. C07C 41/06
[52] U.S. Cl. .................................... 568/697; 502/61; 502/63; 502/64
[58] Field of Search .......................................... 568/697

[56] References Cited

U.S. PATENT DOCUMENTS

| | | | |
|---|---|---|---|
| 4,439,409 | 3/1984 | Puppe et al. | 502/60 |
| 4,859,648 | 8/1989 | Landis et al. | 502/242 |
| 4,954,325 | 9/1990 | Rubin et al. | 423/328 |
| 4,962,239 | 10/1990 | Bell et al. | 568/697 |

Primary Examiner—Howard T. Mars
Attorney, Agent, or Firm—Alexander J. McKillop; Dennis P. Santini; Edward F. Kenehan, Jr.

[57] ABSTRACT

Olefin is etherified with alcohol to provide an ether or mixture of ethers employing a catalyst comprising MCM-36.

16 Claims, 2 Drawing Sheets

PROCESS FOR PREPARING ETHERS

CROSS-REFERENCE TO RELATED APPLICATION

This application is related to copending U.S. Application Ser. No. 07/811,360, filed Dec. 20, 1991, which is a continuation-in-part of copending U.S. Application Ser. No. 07/776,718, filed Oct. 15, 1991, which is a continuation of U.S. Application Ser. No. 07/640,330 filed Jan. 11, 1991, now abandoned.

BACKGROUND

This invention relates to a process for the catalytic reaction of olefin(s) with alcohol(s) to provide ether(s). More particularly, the invention relates to a process for the reaction of one or more light olefins such as ethylene, propylene, butene(s), pentene(s), hexene(s), heptene(s), etc., or mixtures thereof, with one or more lower alkanols, e.g., methanol, ethanol, n-propanol, isopropanol, etc., or mixtures thereof, to provide one or more ethers employing the acidic form of a particular synthetic porous MCM-36 material as catalyst. The product ether(s) are useful, inter alia, as high octane blending stocks for gasoline.

Zeolitic materials, both natural and synthetic, have been demonstrated in the past to have catalytic properties for various types of hydrocarbon conversion. Certain zeolitic materials are ordered, porous crystalline aluminosilicates having a definite crystalline structure as determined by X-ray diffraction, within which there are a large number of smaller cavities which may be interconnected by a number of still smaller channels or pores. These cavities and pores are uniform in size within a specific zeolitic material. Since the dimensions of these pores are such as to accept for adsorption molecules of certain dimensions while rejecting those of larger dimensions, these materials have come to be known as "molecular sieves" and are utilized in a variety of ways to take advantage of these properties. Such molecular sieves, both natural and synthetic, include a wide variety of positive ion-containing crystalline silicates. These silicates can be described as a rigid three-dimensional framework of $SiO_4$ and Periodic Table Group IIIA element oxide, e.g., $AlO_4$, in which the tetrahedra are cross-linked by the sharing of oxygen atoms whereby the ratio of the total Group IIIA element, e.g., aluminum, and silicon atoms to oxygen atoms is 1:2. The electrovalence of the tetrahedra containing the Group IIIA element, e.g., aluminum, is balanced by the inclusion in the crystal of a cation, e.g., an alkali metal or an alkaline earth metal cation. This can be expressed wherein the ratio of the Group IIA element, e.g., aluminum, to the number of various cations, such as Ca/2, Sr/2, Na, K or Li, is equal to unity. One type of cation may be exchanged either entirely or partially with another type of cation utilizing ion exchange techniques in a conventional manner. By means of such cation exchange, it has been possible to vary the properties of a given silicate by suitable selection of the cation. The spaces between the tetrahedra are occupied by molecules of water prior to dehydration.

Prior art techniques have resulted in the formation of a great variety of synthetic zeolites. Many of these zeolites have come to be designated by letter or other convenient symbols, as illustrated by zeolite Z (U.S. Pat. No. 2,882,243), zeolite X (U.S. Pat. No. 2,882,244), zeolite Y (U.S. Pat. No. 3,130,007), zeolite ZK-5 (U.S. Pat. No. 3,247,195), zeolite ZK-4 (U.S. Pat. No. 3,314,752), zeolite ZSM-5 (U.S. Pat. No. 3,702,886), zeolite ZSM-11 (U.S. Pat. No. 3,709,979), zeolite ZSM-12 (U.S. Pat. No. 3,832,449), zeolite ZSM-20 (U.S. Pat. No. 3,972,983), zeolite ZSM-35 (U.S. Pat. No. 4,016,245), and zeolite ZSM-23 (U.S. Pat. No. 4,076,842), merely to name a few.

The $SiO_2/Al_2O_3$ ratio of a given zeolite is often variable. For example, zeolite X can be synthesized with $SiO_2/Al_2O_3$ ratios of from 2 to 3; zeolite Y, from 3 to about 6. In some zeolites, the upper limit of the $SiO_2/Al_2O_3$ ratio is unbounded. ZSM-5 is one such example wherein the $SiO_2/Al_2O_3$ ratio is at least 5 and up to the limits of present analytical measurement techniques. U.S. Pat. No. 3,941,871 (Re. 29,948) discloses a porous crystalline silicate made from a reaction mixture containing no deliberately added alumina in the recipe and exhibiting the X-ray diffraction pattern characteristic of ZSM-5. U.S. Pat. Nos. 4,061,724, 4,073,865 and 4,104,294 describe crystalline silicates of varying alumina and metal content.

There is a need for an efficient catalytic process to manufacture ethers from the reaction of light olefins with lower alkanols augmenting the supply of high octane blending stocks for gasoline. Relatively low molecular weight ethers such as methyl-t-butyl ether (MTBE) and t-amyl methyl ether (TAME) are in the gasoline boiling range and are known to have a high blending octane number. The petrochemicals industry produces mixtures of light olefin streams in the $C_2$ to $C_7$ molecular weight range and the conversion of such streams or fractions thereof to ethers can also provide products useful as solvents and as blending stocks for gasoline. An FCC unit may produce olefins in the gasoline boiling range, e.g., having from 5 to 7 carbon atoms. Such an FCC unit may also produce light olefins having from 2 to 4 carbon atoms.

The reaction of light olefins with lower alkanols to provide ethers is a well known type of process.

According to U.S. Pat. No. 4,042,633, diisopropylether (DIPE) is prepared from isopropyl alcohol (IPA) employing montmorillonite clay catalysts, optionally in the presence of added propylene.

U.S. Pat. No. 4,175,210 discloses the use of silicatungstic acid as catalyst for the reaction of olefin(s) with alcohol(s) to provide ether(s).

As disclosed in U.S. Pat. No. 4,182,914, DIPE is produced from IPA and propylene in a series of operations employing a strongly acidic cation exchange resin as catalyst.

In the process for producing a gasoline blending stock described in U.S. Pat. No. 4,334,890, a mixed $C_4$ stream containing isobutylene is reacted with aqueous ethanol to form a mixture of ethyl tertiary butyl ether and tertiary butanol.

U.S. Pat. No. 4,418,219 describes the preparation of MTBE by reacting isobutylene and methanol in the presence of boron phosphate, blue tungsten oxide or crystalline aluminosilicate zeolite having a silica to alumina mole ratio of at least 12:1 and a constraint index of from 1 to about 12 as catalyst.

U.S. Pat. No. 4,605,787 discloses the preparation of alkyl tert-alkyl ethers such as MTBE and TAME by the reaction of a primary alcohol with an olefin having a double bond on a tertiary carbon atom employing as catalyst an acidic zeolite having a constraint index of from about 1 to 12, e.g., zeolite ZSM-5, 11, 12, 23, dealuminized zeolite Y and rare earth-exchanged zeolite Y.

European Pat. Application 55,045 describes a process for reacting an olefin and an alcohol to provide an ether, e.g., isobutene and methanol to provide MTBE, in the presence of an acidic zeolite such as zeolite Beta, zeolites ZSM-5, -8, -11, -12, -23, -35, -43 and -48, and others, as catalyst.

German Pat. No. 133,661 describes the reaction of isobutene and methanol to provide a mixture of products including MTBE, butanol and isobutene dimer in the presence of acidic zeolite Y as catalyst.

According to Japanese Pat. No. 59-25345, a primary alcohol is reacted with a tertiary olefin in the presence of a zeolite having a silica to alumina mole ratio of at least 10 and the x-ray diffraction disclosed therein to provide a tertiary ether.

U.S. Pat. No. 4,962,239 describes the etherification of olefins with an alcohol over a catalyst comprising a zeolite designated MCM-22.

SUMMARY

There is provided a process for manufacturing an ether or mixture of ethers which comprises reacting at least one olefin with at least one alcohol under etherification reaction conditions to provide at least one ether employing an etherification catalyst composition comprising an acidic synthetic porous material designated MCM-36.

The ether, or mixture of ethers, resulting from the foregoing process are advantageously employed as blending components for gasoline or as cosolvents for methanol to be incorporated into gasoline, among other applications.

EMBODIMENTS

Figure 1:
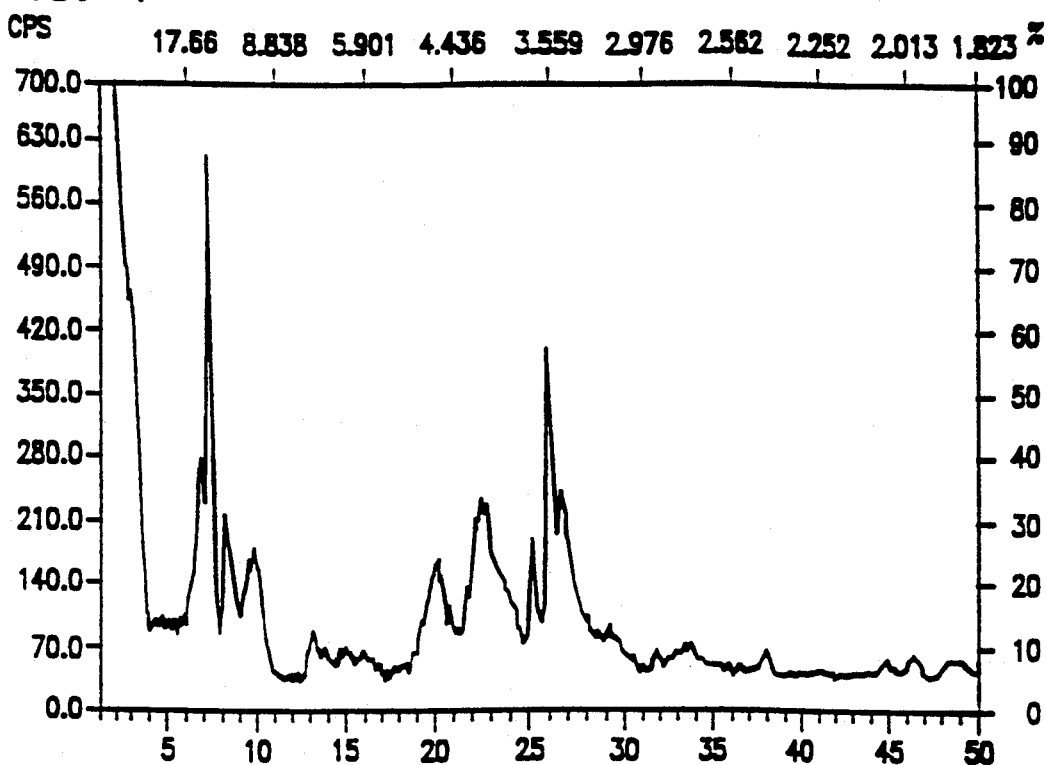
FIG. 1 is an X-ray diffraction pattern of an as-synthesized form of a layered material which may be swollen and pillared.

The present invention is applicable to the reaction of individual olefins and mixtures of olefins, preferably within the $C_{3-10}$ range, with individual alcohols and mixtures of alcohols, preferably those possessing up to about 8 carbon atoms and more preferably those possessing from 1 to 4 carbon atoms. Suitable olefins include propylene, butenes, pentenes, hexenes, heptenes, etc., and mixtures of these and other olefins such as gas plant off-gas containing ethylene and propylene, naphtha cracker off-gas containing light olefins, fluidized catalytic cracked (FCC) light gasoline containing pentenes, hexenes and heptenes, refinery FCC propane/propylene streams, etc. For example, the following composition is typical for an FCC light olefin stream which can be converted to ethers in accordance with this invention:

|  | Wt. % | Mole % |
|---|---|---|
| Ethane | 3.3 | 5.1 |
| Ethylene | 0.7 | 1.2 |
| Propane | 14.5 | 15.3 |
| Propylene | 42.5 | 46.8 |
| Isobutane | 12.9 | 10.3 |
| n-Butane | 3.3 | 2.6 |
| Butenes | 22.1 | 18.32 |
| Pentanes | 0.7 | 0.4 |

Tertiary olefins are preferred as feedstocks herein with isobutene and/or a tertiary pentene being especially preferred.

Suitable alcohols include lower alkanols such as methanol, ethanol, n-propanol, isopropanol, n-butanol, etc., and substituted lower alkanols, e.g., methoxyethanol, etc. Also contemplated are individual alcohols and mixtures of alcohols which are obtained from the catalytic hydration of olefins in accordance with known and conventional processes. Of the alcohols which are suitable for use herein, the primary and secondary alcohols are preferred with methanol being especially preferred.

MCM-36 and methods for its preparation are described in the aforementioned U.S. Application Serial No. 07/811,360, Dec. 20, 1991, the entire disclosure of which is expressly incorporated herein by reference.

MCM-36 may be prepared from an intermediate material which is crystallized in the presence of a hexamethyleneimine directing agent and which, if calcined, without being swollen would be transformed into a material having an X-ray diffraction pattern as shown in Table 1.

TABLE 1

| Interplanar d-Spacing (A) | Relative Intensity, $I/I_o \times 100$ |
|---|---|
| 30.0 ± 2.2 | w-m |
| 22.1 ± 1.3 | w |
| 12.36 ± 0.2 | m-vs |
| 11.03 ± 0.2 | m-s |
| 8.83 ± 0.14 | m-vs |
| 6.86 ± 0.14 | w-m |
| 6.18 ± 0.12 | m-vs |
| 6.00 ± 0.10 | w-m |
| 5.54 ± 0.10 | w-m |
| 4.92 ± 0.09 | w |
| 4.64 ± 0.08 | w |
| 4.41 ± 0.08 | w-m |
| 4.25 ± 0.08 | w |
| 4.10 ± 0.07 | w-s |
| 4.06 ± 0.07 | w-s |
| 3.91 ± 0.07 | m-vs |
| 3.75 ± 0.06 | w-m |
| 3.56 ± 0.06 | w-m |
| 3.42 ± 0.06 | vs |
| 3.30 ± 0.05 | w-m |
| 3.20 ± 0.05 | w-m |
| 3.14 ± 0.05 | w-m |
| 3.07 ± 0.05 | w |
| 2.99 ± 0.05 | w |
| 2.82 ± 0.05 | w |
| 2.78 ± 0.05 | w |
| 2.68 ± 0.05 | w |
| 2.59 ± 0.05 | w |

The values in this Table and like tables presented hereinafter were determined by standard techniques. The radiation was the K-alpha doublet of copper and a diffractometer equipped with a scintillation counter and an associated computer was used. The peak heights, I, and the positions as a function of 2 theta, where theta is the Bragg angle, were determined using algorithms on the computer associated with the diffractometer. From these, the relative intensities, 100 $I/I_o$, where $I_o$ is the intensity of the strongest line or peak, and d (obs.) the interplanar spacing in Angstrom Units (A), corresponding to the recorded lines, were determined. In Tables 1-8, the relative intensities are given in terms of the symbols w=weak, m=medium, s=strong and vs=very strong. In terms of intensities, these may be generally designated as follows:

| w | = | 0-20 |
|---|---|---|
| m | = | 20-40 |
| s | = | 40-60 |
| vs | = | 60-100 |

The material having the X-ray diffraction pattern of Table 1 is known as MCM-22 and is described in U.S. Pat. No. 4,954,325, the entire disclosure of which is incorporated herein by reference. This material can be prepared from a reaction mixture containing sources of alkali or alkaline earth metal (M), e.g., sodium or potassium, cation, an oxide of trivalent element X, e.g., aluminum, an oxide of tetravalent element Y, e.g., silicon, an organic (R) directing agent, hereinafter more particularly described, and water, said reaction mixture having a composition, in terms of mole ratios of oxides, within the following ranges:

| Reactants | Useful | Preferred |
|---|---|---|
| $YO_2/X_2O_3$ | 10-80 | 10-60 |
| $H_2O/YO_2$ | 5-100 | 10-50 |
| $OH^-/YO_2$ | 0.01-1.0 | 0.1-0.5 |
| $M/YO_2$ | 0.01-2.0 | 0.1-1.0 |
| $R/YO_2$ | 0.05-1.0 | 0.1-0.5 |

In the synthesis method for preparing the material having the X-ray diffraction pattern of Table 1, the source of $YO_2$ must be comprised predominately of solid $YO_2$, for example at least about 30 wt.% solid $YO_2$ in order to obtain the desired crystal product. Where $YO_2$ is silica, the use of a silica source containing at least about 30 wt. % solid silica, e.g., Ultrasil (a precipitated, spray dried silica containing about 90 wt. % silica) or HiSil (a precipitated hydrated SiO2 containing about 87 wt. % silica, about 6 wt. % free $H_2O$ and about 4.5 wt. % bound $H_2O$ of hydration and having a particle size of about 0.02 micron) favors crystal formation from the above mixture and is a distinct improvement over the synthesis method taught in U.S. Pat. 4,439,409. If another source of oxide of silicon e.g., Q-Brand (a sodium silicate comprised of about 28.8 wt. % $SiO_2$, 8.9 wt. % $Na_2O$ and 62.3 wt. % $H_2O$) is used, crystallization yields little or none of the crystalline material having the X-ray diffraction pattern of Table 1. Impurity phases of other crystal structures, e.g., ZSM-12, are prepared in the latter circumstance. Preferably, therefore, the $YO_2$, e.g., silica, source contains at least about 30 wt. % solid $YO_2$, e.g., silica, and more preferably at least about 40 wt. % solid $YO_2$, e.g., silica.

Crystallization of the crystalline material having the X-ray diffraction pattern of Table 1 can be carried out at either static or stirred conditions in a suitable reactor vessel, such as for example, polypropylene jars or teflon lined or stainless steel autoclaves. The total useful range of temperatures for crystallization is from about 80° C. to about 225° C. for a time sufficient for crystallization to occur at the temperature used, e.g., from about 24 hours to about 60 days. Thereafter, the crystals are separated from the liquid and recovered.

The organic directing agent for use in synthesizing the present crystalline material from the above reaction mixture may be hexamethyleneimine which has the following structural formula:

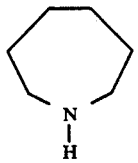

Other organic directing agents which may be used include 1,4-diazacycloheptane, azacyclooctane, aminocyclohexane, aminocycloheptane, aminocyclopentane, N,N,N-trimethyl-1-adamantanammonium ions, and N,N,N-trimethyl-2-adamantanammonium ions. In general, the organic directing agent may be selected from the group consisting of heterocyclic imines, cycloalkyl amines and adamantane quaternary ammonium ions.

It should be realized that the reaction mixture components can be supplied by more than one source. The reaction mixture can be prepared either batchwise or continuously. Crystal size and crystallization time of the crystalline material will vary with the nature of the reaction mixture employed and the crystallization conditions.

Synthesis of crystals may be facilitated by the presence of at least 0.01 percent, e.g., 0.10 percent or 1 percent, seed crystals (based on total weight) of crystalline product.

The crystalline material having the X-ray diffraction pattern of Table 1 passes through an intermediate stage. The material at this intermediate stage has a different X-ray diffraction pattern than that set forth in Table 1. It has further been discovered that this intermediate material is swellable with the use of suitable swelling agents such as cetyltrimethylammonium compounds, e.g., cetyltrimethylammonium hydroxide. However, when this swollen intermediate material is calcined, even under mild conditions, whereby the swelling agent is removed, the material can no longer be swollen with such swelling agent. By way of contrast it is noted that various layered silicates such as magadiite and kenyaite may be swellable with cetyltrimethylammonium compounds both prior to and after mild calcination.

The present swollen products may have relatively high interplanar distance (d-spacing), e.g., greater than about 6 Angstrom, e.g., greater than about 10 Angstrom and even exceeding 30 Angstrom. These swollen materials may be converted into pillared materials. These pillared materials, particularly silica pillared materials, may be capable of being exposed to severe conditions such as those encountered in calcining, e.g., at temperatures of about 450° C. for about two or more hours, e.g., four hours, in nitrogen or air, without significant decrease, e.g., less than about 10%, in interlayer distance.

The material having the X-ray diffraction pattern of Table 1, when intercepted in the swellable, intermediate state, prior to final calcination, may have the X-ray diffraction pattern shown in Table 2.

TABLE 2

| d(A) | I/I$_o$ |
| --- | --- |
| 13.53 ± 0.2 | m-vs |
| 12.38 ± 0.2 | m-vs |
| 11.13 ± 0.2 | w-s |
| 9.15 ± 0.15 | w-s |
| 6.89 ± 0.15 | w-m |
| 4.47 ± 0.10 | w-m |
| 3.95 ± 0.08 | w-vs |
| 3.56 ± 0.06 | w-m |
| 3.43 ± 0.06 | m-vs |
| 3.36 ± 0.05 | w-s |

An X-ray diffraction pattern trace for an example of such an as-synthesized, swellable material is shown in FIG. 1. A particular example of such an as-symthesized, swellable material is the material of Example 1 of the aforementioned U.S. Pat. No. 4,954,325. This material of Example 1 of U.S. Pat. No. , 4,954,325 has the X-ray diffraction pattern given in the following Table 3.

TABLE 3

| 2 Theta | d(A) | I/I$_o$ × 100 |
| --- | --- | --- |
| 3.1 | 28.5 | 14 |
| 3.9 | 22.7 | <1 |
| 6.53 | 13.53 | 36 |
| 7.14 | 12.38 | 100 |
| 7.94 | 11.13 | 34 |
| 9.67 | 9.15 | 20 |
| 12.85 | 6.89 | 6 |
| 13.26 | 6.68 | 4 |
| 14.36 | 6.17 | 2 |
| 14.70 | 6.03 | 5 |
| 15.85 | 5.59 | 4 |
| 19.00 | 4.67 | 2 |
| 19.85 | 4.47 | 22 |
| 21.56 | 4.12 | 10 |
| 21.94 | 4.05 | 19 |
| 22.53 | 3.95 | 21 |
| 23.59 | 3.77 | 13 |
| 24.98 | 3.56 | 20 |
| 25.98 | 3.43 | 55 |
| 26.56 | 3.36 | 23 |
| 29.15 | 3.06 | 4 |
| 31.58 | 2.833 | 3 |
| 32.34 | 2.768 | 2 |
| 33.48 | 2.676 | 5 |
| 34.87 | 2.573 | 1 |
| 36.34 | 2.472 | 2 |
| 37.18 | 2.418 | 1 |
| 37.82 | 2.379 | 5 |

Taking into account certain modifications, this swellable material may be swollen and pillared by methods generally discussed in the aforementioned U.S. Pat. No. 4,859,648, the entire disclosure of which is expressly incorporated herein be reference. The present modifications are discussed hereinafter and include the selection of proper swelling pH and swelling agent.

Upon being swollen with a suitable swelling agent, such as a cetyltrimethylammonium compound, the swollen material may have the X-ray diffraction pattern shown in Table 4.

TABLE 4

| d(A) | I/I$_o$ |
| --- | --- |
| >32.2 | vs |
| 12.41 ± 0.25 | w-s |
| 3.44 ± 0.07 | w-s |

The X-ray diffraction pattern of this swollen material may have additional lines with a d(A) spacing less than the line at 12.41 ±0.25, but none of said additional lines have an intensity greater than the line at the d(A) spacing of 12.41±0.25 or at 3.44±0.07, whichever is more intense. More particularly, the X-ray diffraction pattern of this swollen material may have the lines shown in the following Table 5.

TABLE 5

| d(A) | I/I$_o$ |
| --- | --- |
| >32.2 | vs |
| 12.41 ± 0.25 | w-s |
| 11.04 ± 0.22 | w |
| 9.28 ± 0.19 | w |
| 6.92 ± 0.14 | w |
| 4.48 ± 0.09 | w-m |
| 3.96 ± 0.08 | w-m |
| 3.57 ± 0.07 | w-m |
| 3.44 ± 0.07 | w-s |
| 3.35 ± 0.07 | w |

Even further lines may be revealed upon better resolution of the X-ray diffraction pattern. For example, the X-ray diffraction pattern may have additional lines at the following d(A) spacings (intensities given in parentheses): 16.7±4.0 (w-m); 6.11±0.24 (w); 4.05±0.08 (w); and 3.80±0.08 (w).

In the region with d<9 A, the pattern for the swollen material is essentially like the one given in Table 2 for the unswollen material, but with the possibility of broadening of peaks.

Figure 2:
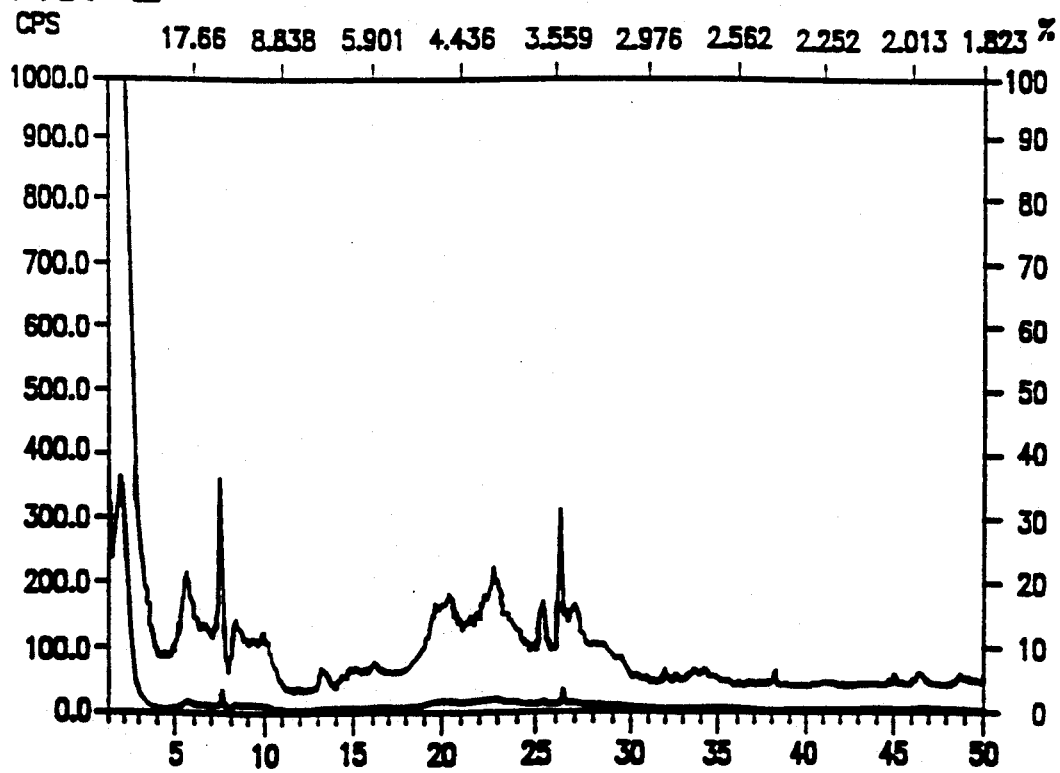
FIG. 2 is an X-ray diffraction pattern of a swollen form of the material having the X-ray diffraction pattern shown in FIG. 1.

An X-ray diffraction pattern trace for an example of such a swollen material is shown in FIG. 2. The upper profile is a 10-fold magnification of the lower profile in FIG. 2.

Upon being pillared with a suitable polymeric oxide, such as polymeric silica, the swollen material having the X-ray diffraction pattern shown in Table 4 may be converted into a material having the X-ray diffraction pattern shown in Table 6.

TABLE 6

| d(A) | I/I$_o$ |
| --- | --- |
| >32.2 | vs |
| 12.38 ± 0.25 | w-m |
| 3.42 ± 0.07 | w-m |

The X-ray diffraction pattern of this pillared material may have additional lines with a d(A) spacing less than the line at 12.38 ±0.25, but none of said additional lines have an intensity greater than the line at the d(A) spacing of 12.38±0.25 or 3.42 ±0.07, whichever is more intense. More particularly, the X-ray diffraction pattern of this pillared material may have the lines shown in the following Table 7.

TABLE 7

| d(A) | I/I$_o$ |
| --- | --- |
| >32.2 | vs |
| 12.38 ± 0.25 | w-m |
| 10.94 ± 0.22 | w-m |
| 9.01 ± 0.18 | w |
| 6.88 ± 0.14 | w |
| 6.16 ± 0.12 | w-m |
| 3.93 ± 0.08 | w-m |
| 3.55 ± 0.07 | w |
| 3.42 ± 0.07 | w-m |
| 3.33 ± 0.07 | w-m |

Even further lines may be revealed upon better resolution of the X-ray diffraction pattern. For example, the X-ray diffraction pattern may have additional lines at the following d(A) spacings (intensities given in parentheses): 5.59±0.11 (w); 4.42±0.09 (w); 4.11±0.08 (w); 4.04±0.08 (w); and 3.76±0.08 (w).

Figure 3:
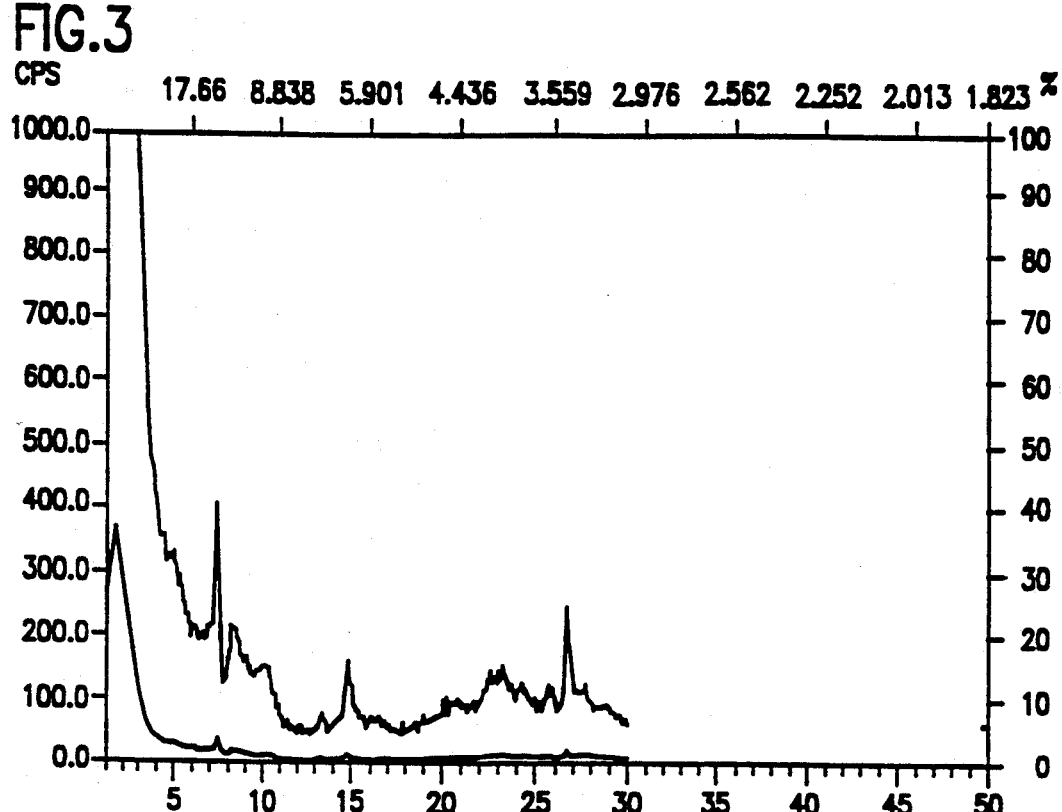
FIG. 3 is an X-ray diffraction pattern of the pillared form of the layered material having the X-ray diffraction pattern shown in FIG. 1.

An X-ray diffraction pattern trace for an example of such a pillared material is given in FIG. 3. The upper profile is a 10-fold magnification of the lower profile in FIG. 3.

If the material swollen with a suitable swelling agent is calcined without prior pillaring another material is produced. For example, if the material which is swollen but not pillared is calcined in air for 6 hours at 540° C., a very strong line at a d(A) spacing of greater than 32.2 will no longer be observed. By way of contrast, when the swollen, pillared material is calcined in air for 6 hours at 540° C., a very strong line at a d(A) spacing of greater than 32.2 will still be observed, although the precise position of the line may shift.

An example of a swollen, non-pillared material, which has been calcined, has the pattern as shown in Table 8.

TABLE 8

| 2 Theta | d(A) | $I/I_o \times 100$ | |
|---|---|---|---|
| 3.8 | 23.3 | 12 | |
| 7.02 | 12.59 | 100 | |
| 8.02 | 11.02 | 20 | |
| 9.66 | 9.16 | 14 | |
| 12.77 | 6.93 | 7 | |
| 14.34 | 6.18 | 45 | |
| 15.75 | 5.63 | 8 | |
| 18.19 | 4.88 | 3 | |
| 18.94 | 4.69 | 3 | |
| 19.92 | 4.46 | 13 | broad |
| 21.52 | 4.13 | 13 | shoulder |
| 21.94 | 4.05 | 18 | |
| 22.55 | 3.94 | 32 | |
| 23.58 | 3.77 | 16 | |
| 24.99 | 3.56 | 20 | |
| 25.94 | 3.43 | 61 | |
| 26.73 | 3.33 | 19 | |
| 31.60 | 2.831 | 3 | |
| 33.41 | 2.682 | 4 | |
| 34.62 | 2.591 | 3 | broad |
| 36.36 | 2.471 | 1 | |
| 37.81 | 2.379 | 4 | |

The X-ray powder pattern shown in Table 8 is similar to that shown in Table 1 except that most of the peaks in Table 8 are much broader than those in Table 1.

Figure 4:
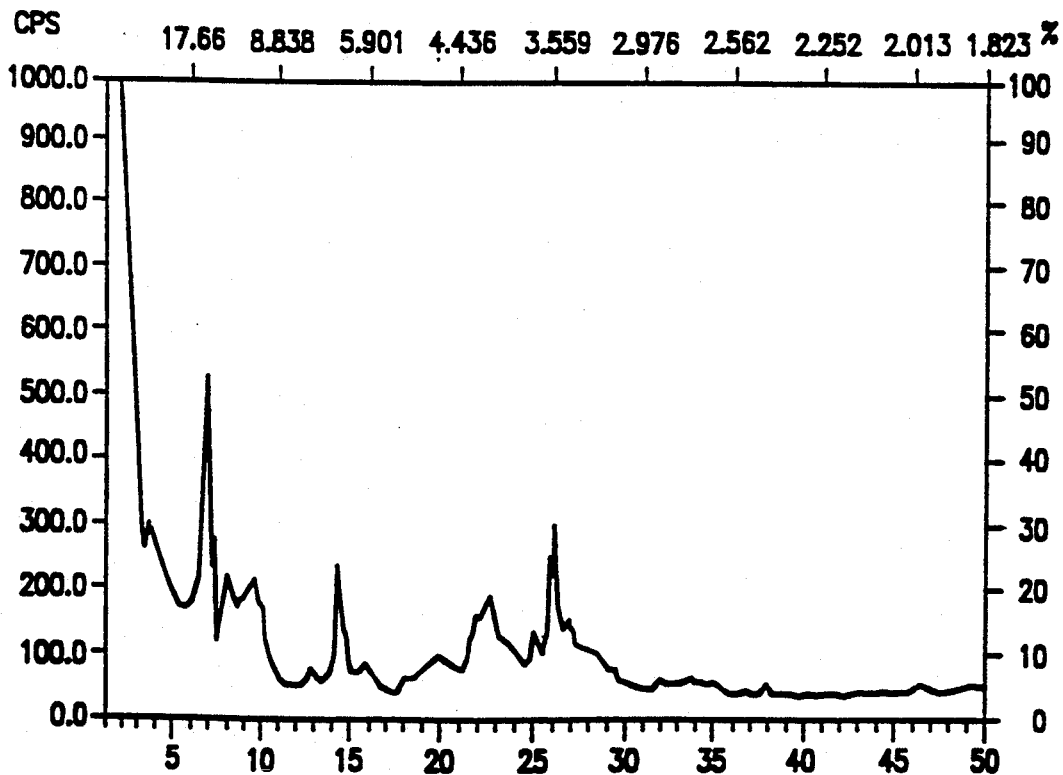
FIG. 4 is an X-ray diffraction pattern of the calcined form of the swollen material having the X-ray diffraction pattern shown in FIG. 2.

An X-ray diffraction pattern trace for an example of the calcined material corresponding to Table 8 is given in FIG. 4.

As mentioned previously, the calcined material corresponding to the X-ray diffraction pattern of Table 1 is designated MCM-22. For the purposes of the present disclosure, the pillared material corresponding to the X-ray diffraction pattern of Table 6 is designated herein as MCM-36. The swollen material corresponding to the X-ray diffraction pattern of Table 4 is designated herein as the swollen MCM-22 precursor. The as-synthesized material corresponding to the X-ray diffraction pattern of Table 2 is referred to herein, simply, as the MCM-22 precursor.

The layers of the swollen material of this disclosure may have a composition involving the molar relationship:

$X_2O_3$:(n)$YO_2$,ps wherein X is a trivalent element, such as aluminum, boron, iron and/or gallium, preferably aluminum, Y is a tetravalent element such as silicon and/or germanium, preferably silicon, and n is at least about 5, usually from about 10 to about 150, more usually from about 10 to about 60, and even more usually from about 10 to about 40.

To the extent that the layers of the swollen MCM-22 precursor and MCM-36 have negative charges, these negative charges are balanced with cations. For example, expressed in terms of moles of oxides, the layers of the swollen MCM-22 precursor and MCM-36 may have a ratio of 0.5 to 1.5 $R_2O:X_2O_3$, where R is a monovalent cation or 1/m of a cation of valency m.

MCM-3 adsorbs significant amounts of commonly used test adsorbate materials, i.e., cyclohexane, n-hexane and water. Adsorption capacities for this pillared material, especially the silica pillared material, may range at room temperature as follows:

| Adsorbate | Capacity, Wt. Percent |
|---|---|
| n-hexane | 17-40 |
| cyclohexane | 17-40 |
| water | 10-40 | wherein cyclohexane and n-hexane sorption are measured at 20 Torr and water sorption is measured at 12 Torr.

The swellable material, used to form the swollen material of the present disclosure, may be initially treated with a swelling agent. Such swelling agents are materials which cause the swellable layers to separate by becoming incorporated into the interspathic region of these layers. The swelling agents are removable by calcination, preferably in an oxidizing atmosphere, whereby the swelling agent becomes decomposed and/or oxidized.

Suitable swelling agents may comprise a source of organic cation, such as quaternary organoammonium or organophosphonium cations, in order to effect an exchange of interspathic cations. Organoammonium cations, such as n-octylammonium, showed smaller swelling efficiency than, for example, cetyltrimethylammonium. A pH range of 11 to 14, preferably 12.5 to 13.5 is generally employed during treatment with the swelling agent.

The as-synthesized material is preferably not dried prior to being swollen. This as-synthesized material may be in the form of a wet cake having solids content of less than 30% by weight, e.g., 25 wt % or less.

The foregoing swelling treatment results in the formation of a layered oxide of enhanced interlayer separation depending upon the size of the organic cation introduced. In one embodiment, a series of organic cation exchanges can be carried out. For example, an organic cation may be exchanged with an organic cation of greater size, thus increasing the interlayer separation in a step-wise fashion. When contact of the layered oxide with the swelling agent is conducted in aqueous medium, water is trapped between the layers of the swollen species.

The organic-swollen species may be treated with a compound capable of conversion, e.g., by hydrolysis and/or calcination, to pillars of an oxide, preferably to a polymeric oxide. Where the treatment involves hydrolysis, this treatment may be carried out using the water already present in organic-swollen material. In this case, the extent of hydrolysis may be modified by varying the extent to which the organic-swollen species is dried prior to addition of the polymeric oxide precursor.

It is preferred that the organic cation deposited between the layers be capable of being removed from the pillared material without substantial disturbance or removal of the interspathic polymeric oxide. For example, organic cations such as cetyltrimethylammonium may be removed by exposure to elevated temperatures, e.g., calcination, in nitrogen or air, or by chemical oxidation preferably after the interspathic polymeric oxide precursor has been converted to the polymeric oxide pillars in order to form the pillared layered product.

These pillared layered products, especially when calcined, exhibit high surface area, e.g., greater than 500 $m^2/g$, and thermal and hydrothermal stability making them highly useful as catalysts or catalytic supports, for hydrocarbon conversion processes, for example, alkylation.

Insertion of the organic cation between the adjoining layers serves to physically separate the layers in such a way as to make the layered material receptive to the interlayer addition of a polymeric oxide precursor. In particular, cetyltrimethylammonium cations have been found useful. These cations are readily incorporated within the interlayer spaces of the layered oxide serving to prop open the layers in such a way as to allow incorporation of the polymeric oxide precursor. The extent of the interlayer spacing can be controlled by the size of the organoammonium ion employed.

Interspathic oxide pillars, which may be formed between the layers of the propped or swollen oxide material, may include an oxide, preferably a polymeric oxide, of zirconium or titanium or more preferably of an element selected from Group IVB of the Periodic Table (Fischer Scientific Company Cat. No. 5-702-10, 1978), other than carbon, i.e., silicon, germanium, tin and lead. Other suitable oxides include those of Group VA, e.g., V, Nb, and Ta, those of Group IIA, e.g., Mg or those of Group IIIB, e.g., B. Most preferably, the pillars include polymeric silica. In addition, the oxide pillars may include an element which provides catalytically active acid sites in the pillars, preferably aluminum.

The oxide pillars are formed from a precursor material which may be introduced between the layers of the organic "propped" species as an ionic or electrically neutral compound of the desired elements, e.g., those of Group IVB. The precursor material may be an organometallic compound which is a liquid under ambient conditions. In particular, hydrolyzable compounds, e.g., alkoxides, of the desired elements of the pillars may be utilized as the precursors. Suitable polymeric silica precursor materials include tetraalkylsilicates, e.g., tetrapropylorthosilicate, tetramethylorthosilicate and, most preferably, tetraethylorthosilicate. Suitable polymeric silica precursor materials also include quaternary ammonium silicates, e.g., tetramethylammonium silicate (i.e. TMA silicate). Where the pillars also include polymeric alumina, a hydrolyzable aluminum compound can be contacted with the organic "propped" species before, after or simultaneously with the contacting of the propped layered oxide with the silicon compound. Preferably, the hydrolyzable aluminum compound employed is an aluminum alkoxide, e.g., aluminum isopropoxide. If the pillars are to include titania, a hydrolyzable titanium compound such as titanium alkoxide, e.g., titanium isopropoxide, may be used.

After calcination to remove the organic propping agent, the final pillared product may contain residual exchangeable cations. Such residual cations in the layered material can be ion exchanged by known methods with other cationic species to provide or alter the catalytic activity of the pillared product. Suitable replacement cations include cesium, cerium, cobalt, nickel, copper, zinc, manganese, platinum, lanthanum, aluminum, ammonium, hydronium and mixtures thereof.

Particular procedures for intercalating layered materials with metal oxide pillars are described in U.S. Pat. Nos. 4,831,005; 4,831,006; and 4,929,587. The entire disclosures of these patents are expressly incorporated herein by reference. U.S. 4,831,005 describes plural treatments with the pillar precursor. U.S. 4,929,587 describes the use of an inert atmosphere, such as nitrogen, to minimize the formation of extralaminar polymeric oxide during the contact with the pillar precursor. U.S. 4,831,006 describes the use of elevated temperatures during the formation of the pillar precursor.

The resulting pillared products exhibit thermal stability at temperatures of 450° C. or even higher as well as substantial sorption capacities (as much as 17 to 40 wt% for $C_6$ hydrocarbon). The pillared products may possess a basal spacing of at least about 32.2A and surface areas greater than 500 $m^2/g$.

The layered material may be subjected to thermal treatment, e.g., to decompose organoammonium ions. This thermal treatment is generally performed by heating one of these forms at a temperature of at least about 370° C. for at least 1 minute and generally not longer than 20 hours. While subatmospheric pressure can be employed for the thermal treatment, atmospheric pressure is preferred simply for reasons of convenience.

Prior to its use as etherification catalyst, the MCM-36 crystals should be subjected to thermal treatment to remove part or all of any organic constituent present therein.

The MCM-36 etherification catalyst herein can also be used in intimate combination with another component having etherification catalystic activity, e.g., any of the known catalysts referred to above.

The catalyst described herein can optionally be used in intimate combination with a hydrogenating component such as tungsten, vanadium, molybdenum, rhenium, nickel, cobalt, chromium, manganese, or a noble metal, such as platinum or palladium. Such a hydrogenation-dehydrogenation component can be associated chemically and/or physically with the MCM-36 and/or matrix with which the MCM-36 may be optionally composited. Thus, e.g., the hydrogenating component can be introduced into the catalyst composition by way of co-crystallization, exchanged into the composition to the extent a Group IIIA element, e.g., aluminum, is in the structure, impregnated therein or intimately physically admixed therewith. Such component can be impregnated in, or on, the MCM-36 such as, for example, by, in the case of platinum, treating the MCM-36 with a solution containing the platinum metal-containing ion. Thus, suitable platinum compounds for this purpose include chloroplatinic acid, platinous chloride and various compounds containing the platinum amine complex.

The MCM-36, especially in its metal, hydrogen and ammonium forms, can be beneficially converted to another form by thermal treatment. This thermal treatment is generally performed by heating one of these forms at a temperature of at least about 370° C. for at least 1 minute and generally not longer than 20 hours. While subatmospheric pressure can be employed for the thermal treatment, atmospheric pressure is preferred simply for reasons of convenience. The thermal treatment can be performed at a temperature of up to about 925° C.

Prior to its use in the etherification process of this invention, the MCM-36 should be dehydrated, at least partially. This can be done by heating the MCM-36 to a temperature in the range of from about 200° C. to about 595° C. in an inert atmosphere, such as air, nitrogen, etc. and at atmospheric, subatmospheric or superatmospheric pressures for between about 30 minutes to about 48 hours. Dehydration can also be performed at room temperature merely by placing the MCM-36 in a vacuum, but a longer time is required to obtain a sufficient amount of dehydration.

The MCM-36 can be shaped into a wide variety of particle sizes. Generally speaking, the particles can be in the form of a powder, a granule, or a molded product such as an extrudate having a particle size sufficient to pass through a 2 mesh (Tyler) screen and be retained on a 400 mesh (Tyler) screen. In cases where the catalyst is molded, such as by extrusion, the MCM-36 can be extruded before drying or partially dried and then extruded.

It may be desired to incorporate the MCM-36 with another material which is resistant to the temperatures and other conditions employed in the etherification process of this invention. Such materials include active and inactive materials and synthetic or naturally occurring zeolites as well as inorganic materials such as clays, silica and/or metal oxides such as alumina. The latter may be either naturally occurring or in the form of gelatinous precipitates or gels including mixtures of silica and metal oxides. Use of a material in conjunction with MCM-36, i.e., combined therewith or present during its synthesis, which itself is catalytically active may change the conversion and/or selectivity of the catalyst. Inactive materials suitably serve as diluents to control the amount of conversion so that ether products can be obtained economically and orderly without employing other means for controlling the rate of reaction. These materials may be incorporated into naturally occurring clays, e.g., bentonite and kaolin, to improve the crush strength of the catalyst under commercial etherification operating conditions. Said materials, i.e., clays, oxides, etc., function as binders for the catalyst. It is desirable to provide a catalyst having good crush strength because in commercial use, it is desirable to prevent the catalyst from breaking down into powderlike materials. These clay binders have been employed normally only for the purpose of improving the crush strength of the catalyst.

Naturally occurring clays which can be composited with MCM-36 include the montmorillonite and kaolin family, which families include the subbentonites, and the kaolins commonly known as Dixie, McNamee, Georgia and Florida clays or others in which the main mineral constituent is halloysite, kaolinite, dickite, nacrite, or anauxite. Such clays can be used in the raw state as originally mined or initially subjected to calcination, acid treatment or chemical modification. Binders useful for compositing with MCM-36 also include inorganic oxides, notably alumina.

In addition to the foregoing materials, the MCM-36 can be composited with a porous matrix material such as silica-alumina, silica-magnesia, silica-zirconia, silica-thoria, silica-beryllia, silica-titania as well as ternary compositions such as silica-alumina-thoria, silica-alumina-zirconia silica-alumina-magnesia and silica-magnesia-zirconia.

The relative proportions of finely divided MCM-36 and inorganic oxide matrix vary widely, with the crystal content ranging from about 1 to about 90 percent by weight and more usually, particularly when the composite is prepared in the form of beads, in the range of about 2 to about 80 weight percent of the composite.

The operating conditions of the etherification process herein are not especially critical and can include a temperature of from about 20° to about 200° C., preferably from about 50° to about 160° C. and most preferably from about 60° to about 120° C., a total system pressure of from about 1 to about 200 atmospheres, preferably from about 3 to about 80 atmospheres and most preferably from about 10 to about 15 atmospheres and an alcohol to olefin to alcohol mole ratio of from about 0.1 to about 5, preferably from about 0.2 to about 2 and most preferably from about 0.5 to about 1.2.

The etherification process of this invention can be carried out under liquid phase, vapor phase or mixed vapor/liquid phase conditions in batch or continuous manner using a stirred tank reactor or fixed bed flow reactor, e.g., trickle-bed, liquid-up-flow, liquid-down-flow, counter-current, co-current, etc. Reaction times of from about 20 minutes to about 20 hours when operating in batch and an WHSV (gram-olefin per hour gram MCM-36) of from about 0.1 to about 200 hr $^{-1}$, preferably from about 0.5 to about 50 hr $^{-1}$ and most preferably from about 1 to about 30 hr $^{-1}$, when operating continuously are suitable. It is generally preferably to recover any unreacted olefin and/or alcohol and recycle same to the reactor.

In order to more fully illustrate the etherification process of this invention, the following examples are presented. In Examples illustrative of the synthesis of zeolite, whenever sorption data are set forth for comparison of sorptive capacities for water, cyclohexane and/or n-hexane, they were Equilibrium Adsorption values determined as follows:

A weighed sample of the calcined adsorbent was contacted with the desired pure adsorbate vapor in an adsorption chamber, evacuated to less than 1 mm Hg and contacted with 12 Torr of water vapor or 40 Torr of n-hexane or 40 Torr of cyclohexane vapor, pressures less than the vapor-liquid equilibrium pressure of the respective adsorbate at 90° C.. The pressure was kept constant (within about ±0.5 mm Hg) by addition of adsorbate vapor controlled by a manostat during the adsorption period, which did not exceed about 8 hours. As adsorbate was adsorbed by the absorbent, the decrease in pressure caused the manostat to open a valve which admitted more adsorbate vapor to the chamber to restore the above control pressures. Sorption was complete when the pressure change was not sufficient to activate the manostat. The increase in weight was calculated as the adsorption capacity of the sample in g/100 g of calcined adsorbant.

EXAMPLE 1

A material which may be swollen and pillared was prepared as follows. Water, sodium hydroxide, sodium aluminate, silica (Ultrasil), and hexamethyleneimine (HMI) were combined in the following mole ratios:

2.5 $Na_2O$:$Al_2O_3$:30 $SiO_2$:10 HMI: 580 $H_2O$.

The reaction mixture was heated in an autoclave to 143° C. for 96 hours. The X-ray diffraction pattern for this material is shown pictorially in FIG. 1.

A mixture of 150 g of the wet cake (42% solids) and 1100 ml of 29% CTMA-OH (a 29% solution of cetyltrimethylammonium chloride that was contacted with hydroxide-for-halide exchange resin-one liter of the resin with 1.4 miliequivalent/ml exchange capacity per liters of the solution) was reacted for 96 hours in a steambox. The product was filtered, washed twice with 400 ml of water and air dried overnight, yielding approximately 101 g of swollen product. Fifty grams of the swollen material was slurried with 300 g of TEOS and heated at 80° C. for 24 hours under a stream of nitrogen. After filtration and overnight drying, the product (56.60 g) was hydrolyzed in water for 4 hours, giving the pillared material (approximately 5 grams) containing 70% solids (based upon calcination at 540° C.). A portion (44.3 grams) of the pillared material was mixed with 23.3 g of Kaiser alumina (72.5% solids) and pelletized. The pellets were exchanged four times with 1 M ammonium nitrate (one hour contact followed by washing with 300 ml of water). The product was reformulated into pellets, dried at 110° C. for two hours and calcined in nitrogen for 3 hours and in air for 6 hours. Total product yield was approximately 41 grams of 65% MCM-36/35% $Al_2O_3$.

EXAMPLE 2

FCC gasoline etherification was performed in a fixed bed reactor, using the alumina-bound MCM-36 catalyst of Example 1. In a ¼" I.D. stainless steel reactor, 8 g of catalyst (14/24 mesh) were heated at 400° F. at 400 psig under nitrogen and maintained under these conditions for 16 hours, after which time the temperature was decreased to 200.F. The hydrocarbon feed, a $C_5-215°$ F. FCC gasoline, was dried over magnesium sulfate, then blended with methanol (75 wt% hydrocarbon/25 wt% absolute alcohol). To commence the reaction, the nitrogen flow to the reactor was stopped and the FCC gasoline/methanol blend was charged at a rate of 3.0 g of liquid per gram of MCM-36 per hour. The total liquid product was contacted with water to remove unreacted methanol from the hydrocarbons. During this water treatment, however, the $C_4-$ and $C_5$ paraffin concentrations decreased, probably due to evaporative losses.

Data from this reaction are given in Table 9. As shown in Table 9, relatively mild conditions (200° F., 400 psig, and 3 WHSV) were employed to convert significant amounts of branched olefins in FCC gasoline to methyl ethers.

TABLE 9

Etherification of $C_5-215°$ F. FCC Gasoline
(75 wt. % Gasoline/25 wt. % Methanol Feed)

|  | Feed | Reaction Product |
|---|---|---|
| Temperature, °F. |  | 200 |
| Pressure, psig |  | 400 |
| Total Feed Rate, WHSV |  | 3.0 |
| Composition, wt. % |  |  |
| Total $C_4-$ | 4.4 | 2.9 |
| Branched $C_5$ Olefins | 9.8 | 3.9 |
| Linear $C_5$ Olefins | 8.4 | 8.3 |
| $C_5$ Paraffins, Others | 16.8 | 15.6 |
| Branched $C_6$ Olefins | 10.2 | 7.7 |
| Linear $C_6$ Olefins | 5.7 | 5.9 |
| $C_6$ Paraffins, Others | 18.8 | 19.8 |
| Total $C_7+$ | 25.9 | 26.6 |
| Methyl $C_5$ Ether (TAME) |  | 5.0 |
| Methyl $C_6$ Ethers |  | 2.0 |
| Methyl $C_7$ Ethers |  | 1.7 |

EXAMPLE 3

The catalyst of Example 1 was used to prepare MTBE. Batch etherification experiments were conducted using the following procedure. The catalyst, in extrudate form, was crushed to a fine powder. In a 300 cc autoclave, 102.8 g of methanol and enough catalyst to provide 5.0 g of MCM-36 were combined. Following a successful pressure test, 150 cc of isobutylene were charged into the reactor and the pressure increased to 200 psig. The temperature within the autoclave was then increased at a rate of 5° F./minute to 150° F. Samples of the liquid inside the reactor were obtained one hour after completing the temperature ramp. Analysis of the aliquots by gas chromatography was used to determine the extent of reaction.

Results are given in Table 10.

EXAMPLE 4

The catalyst of Example 1 was used to prepare TAME. Batch experiments were conducted using the following procedure. A blend of branched $C_5$ olefins, n-pentane, and absolute methanol was used as starting material. In a clean 600 cc autoclave, 1.54 g of catalyst (1.0 g of MCM-36) and 150cc of starting material were combined and the system was pressure tested. Since some evaporation of hydrocarbons occurred during the loading and pressure testing procedures, a small sample of liquid was retrieved prior to the commencement of the reaction. The autoclave was heated to 200° F. at a rate of 8° F./minute, with the reactor pressure reaching a maximum of 220 psig. Two hours after the initiation of heating, a sample of liquid was drawn off. The liquid sample was analyzed by gas chromatography to determine the extent of reaction over MCM-36.

Results ar given in Table 11.

TABLE 10

MTBE Production Over MCM-36
(Batch Reaction, 150° F., 400 psig, 1 HOS)

| Catalyst | MCM-36 |
|---|---|
| Isobutylene Conv. (wt %) | 13 |

TABLE 11

TAME Production over MCM-36
(Batch Reaction, 200° F., 220 psig, 2 HOS)

|  | MCM-36 | |
|---|---|---|
|  | Initial Conc. (wt %) | Final Conc. (wt %) |
| Methanol | 25.8 | 23.5 |
| 2-Methyl-1-butene | 6.1 | 2.3 |
| n-Pentane | 55.9 | 55.9 |
| 2-Methyl-2-butene | 12.2 | 11.1 |
| TAME | 0.0 | 7.3 |

What is claimed is:

1. A process for manufacturing an ether or mixture of ethers which comprises reacting at least one olefin with at least one alcohol under etherification reaction conditions to provide at least one ether employing an etherification catalyst composition comprising an acidic synthetic porous material designated as MCM-36, said MCM-36 being a pillared layered material having the following X-ray diffraction pattern

| d(A) | I/I$_o$ |
|---|---|
| >32.2 | vs |
| 12.38 ± 0.25 | w-m |
| 3.42 ± 0.07 | w-m |

2. A process according to claim 1, wherein the layers of the MCM-36 have a composition comprising the molar relationship $$X_2O_3:(n)YO_2,$$

wherein n is at least about 5, X is a trivalent element selected from the group consisting of aluminum, boron, gallium and combinations thereof, and Y is a tetravalent element selected from the group consisting of silicon, germanium and combinations thereof.

3. A process according to claim 2, wherein X comprises aluminum and Y comprises silicon.

4. A process according to claim 1, wherein the olefin possesses 3 to 10 carbon atoms.

5. A process according to claim 4, wherein the olefin is one olefin or a mixture of olefins selected from the group consisting of propylene, one or more butenes, one or more pentenes, one or more hexenes and one or more heptenes.

6. A process according to claim 1, wherein the alcohol possesses up to 8 carbon atoms.

7. A process according to claim 6, wherein the alcohol is a primary or secondary alkanol.

8. A process according to claim 7, wherein the alcohol is methanol, ethanol, n-propanol, isopropanol or a butanol or a mixture of any of the foregoing.

9. A process according t claim 1, wherein an FCC gasoline fraction having a boiling point of 215° F. or less and methanol are contacted with said MCM-36, said FCC gasoline fraction comprising at least one olefin.

10. A process according to claim 1, wherein the etherification reaction conditions include a temperature of from about 20° to about 200° C., a total system pressure of from about 1 to about 200 atmospheres, an alcohol to olefin mole ratio of from about 0.1 to about 5 and a WHSV of from 0.1 to about 200 hr$^{-1}$.

11. A process according to claim 9, wherein said FCC gasoline fraction comprises olefins having from 4 to 7 carbon atoms.

12. A process according to claim 1, wherein isobutene or isopentene is reacted with methanol.

13. A process according to claim 10, wherein isobutene is reacted with methanol.

14. A process according to claim 10, wherein isopentene is reacted with methanol.

15. A process according to claim 4, wherein the olefin is a tertiary olefin.

16. A process according to claim 15, wherein the tertiary olefin is isobutene or isopentene.

* * * * *